US010583316B1

(12) United States Patent
Cantu et al.

(10) Patent No.: US 10,583,316 B1
(45) Date of Patent: Mar. 10, 2020

(54) SYSTEM FOR AUTOMATICALLY REGULATING BREATHING AIR SUPPLY AND DATA LOGGING

(71) Applicants: Robert Cantu, Houston, TX (US); Christopher Staples, Houston, TX (US)

(72) Inventors: Robert Cantu, Houston, TX (US); Christopher Staples, Houston, TX (US)

(*) Notice: Subject to any disclaimer, the term of this patent is extended or adjusted under 35 U.S.C. 154(b) by 0 days.

(21) Appl. No.: 16/528,341

(22) Filed: Jul. 31, 2019

Related U.S. Application Data

(60) Provisional application No. 62/721,161, filed on Aug. 22, 2018.

(51) Int. Cl.
*G08B 17/10* (2006.01)
*A62B 9/02* (2006.01)
(Continued)

(52) U.S. Cl.
CPC ............. *A62B 9/02* (2013.01); *A62B 9/006* (2013.01); *A62B 9/04* (2013.01); *A61M 16/0627* (2014.02)

(58) Field of Classification Search
CPC .......... A61B 5/01; A61B 5/14532; A61B 2560/0412; A61B 2562/02; A61B 5/0008; A61B 5/0042; A61B 5/0046; A61B 5/0075; A61B 5/0077; A61B 5/0079; A61B 5/015; A61B 5/1176; A61B 5/14546; A61B 5/14551; A61B 5/1491; A61B 5/4064; A61B 5/4076; A61B 5/412; A61B 5/6803; A61B 5/6814; A61B 5/6821; A61B 5/6891; A61B 5/6898; A61B 5/7246; A61B 5/7282; A61B 5/742; A61B 5/746; A61B 17/00491; A61B 17/0057; A61B 17/12022; A61B 17/12118; A61B 17/12181; A61B 17/3468; A61B 18/02; A61B 18/04; A61B 18/1492; A61B 18/18; A61B 18/245;
(Continued)

(56) References Cited

U.S. PATENT DOCUMENTS

7,658,891 B1 * 2/2010 Barnes ............... A61L 9/015
128/205.28
10,420,965 B1 * 9/2019 Dykes ............... A42B 3/225
(Continued)

*Primary Examiner* — Daniel Previl
(74) *Attorney, Agent, or Firm* — Nolte Intellectual Property Law Group (57) ABSTRACT

A system to regulate breathing air of a plurality of sealing and locking helmets and a plurality of supplied air respirators producing a plurality of lower pressure air supply of a plurality of people simultaneously using air regulators, valves, pressure sensors and a temperature sensor that measures temperature in the air module. The system includes a plurality of temperature sensors of measuring temperature of environment around each person of one of the sealing and locking helmets or supplied air respirators, a gas analyzer, an air module processor to control the valves, receiving data from the pressure sensors, controlling lower pressure air supply and presenting data on a display with real time updates that are presented in less than a few milliseconds providing a continuously imported status that achieves safe entry in a hazardous area with fewer accidents by operators, cleaning crew, inspectors, welders, installers, and loaders.

19 Claims, 9 Drawing Sheets

(51) Int. Cl.
*A62B 9/04* (2006.01)
*A62B 9/00* (2006.01)
*A61M 16/06* (2006.01)

(58) Field of Classification Search
CPC ........... A61B 2017/00411; A61B 2017/00544; A61B 2017/0065; A61B 2017/00809; A61B 2017/00876; A61B 2017/1205; A61B 2017/22001; A61B 2018/00005; A61B 2018/00023; A61B 2018/00345; A61B 2018/00517; A61B 2018/00541; A61B 2018/00577; A61B 2018/00595; A61B 2018/00982; A61B 2018/1861; A61B 2218/002; A61B 2503/40; A61B 5/0022; A61B 5/0205; A61B 5/024; A61B 5/02438; A61B 5/076; A61B 5/0816; A61B 5/11; A61B 5/14542; A61B 5/682; B60H 1/00735; B60H 1/00742; G01J 2005/0077; G01J 5/10; H04N 5/2256; H04N 5/33; H04N 7/18; G05B 13/028; G05B 19/4183; G05B 19/4184; G05B 19/41845; G05B 19/4185; G05B 19/41865; G05B 19/41875; G05B 2219/32287; G05B 2219/35001; G05B 2219/37337; G05B 2219/37351; G05B 2219/37434; G05B 2219/40115; G05B 2219/45004; G05B 2219/45129; G05B 23/0221; G05B 23/0229; G05B 23/024; G05B 23/0264; G05B 23/0283; G05B 23/0286; G05B 23/0289; G05B 23/0291; G05B 23/0294; G05B 23/0297; G06K 9/6263; G06K 9/00624; G06K 9/00832; G06K 19/0717; G06K 9/00362; G06K 7/10178; G06N 20/00; G06N 3/02; G06N 5/046; G06N 7/005; G06N 3/006; G06N 3/0445; G06N 3/0454; G06N 3/0472; G06N 3/084; G06N 3/088; G06N 3/126; H04B 17/309; H04B 17/318; H04L 1/0002; H04L 1/0041; H04L 1/18; H04L 5/0064; H04L 67/1097; H04L 67/12; Y02P 80/114; Y02P 90/02; Y02P 20/152; B60N 2/002; B60N 2002/0272; B60N 2002/0268; B60N 2/015; B60N 2/0232; B60N 2/0244; B60N 2/0248; B60N 2/0252; B60N 2/0276; B60N 2/067; B60N 2/28; B60N 2/2806; B60N 2/2863; B60N 2/66; B60N 2/829; B60N 2/853; B60N 2/888; B60R 21/013; B60R 21/01516; B60R 21/0152; B60R 21/0153; B60R 21/01542; B60R 2021/23153; B60R 21/0136; B60R 21/01534; B60R 21/01536; B60R 16/037; B60R 2001/1223; B60R 2001/1253; B60R 2021/0027; B60R 2021/01088; B60R 2021/01184; B60R 2021/01315; B60R 2021/26094; B60R 2021/2765; B60R 2022/208; B60R 2022/288; B60R 2022/4685; B60R 2022/4825; B60R 21/0132; B60R 21/0134; B60R 21/015; B60R 21/01532; B60R 21/01538; B60R 21/01544; B60R 21/01546; B60R 21/01548; B60R 21/01552; B60R 21/01554; B60R 21/203; B60R 21/21656; B60R 21/276; B60R 22/20; B60R 22/201; B60R 25/25; B60R 25/252; B60R 25/255; B60R 25/257; B60R 2021/0004; B60R 2021/23107; B60R 2021/23161; B60R 2021/23169; B60R 2021/23519; B60R 2021/23523; B60R 2021/23557; B60R 2021/2358; B60R 2021/2359; B60R 21/20; B60R 21/213; B60R 21/232; B60R 21/233; B60R 21/235; B60R 21/30; G07C 5/008; G07C 5/0808; G07C 5/085; B60C 11/24; B60C 19/00; B60C 23/0408; B60C 23/005; B60C 23/20; B60C 23/041; B60C 23/0411; B60C 23/0449; B60C 23/12; G01S 13/04; G01S 15/04; G01S 15/06; G01S 15/87; G01S 15/88; G01S 17/88; G01S 17/89; G01S 7/417; G01S 7/4802; G01S 7/539; G01S 15/42; G01S 17/026; B60K 28/06; B60Q 1/143; B60Q 2300/41; B60Q 2300/42; B60T 7/14; B60W 2040/0818; B60W 2540/26; E05F 15/43; E05F 15/431; E05F 2015/433; E05Y 2900/516; E05Y 2900/542; E05Y 2900/55; G06F 3/0219; G06F 3/0233; G06F 3/0237; G06F 3/0238; G08B 13/1427; G08B 13/248; G08B 21/0286; G08B 29/181; G08G 1/017; G08G 1/164; G10K 2210/1282; G10K 2210/3219; H01Q 1/3291; H01Q 1/22; H01Q 1/2241; A61F 2002/9528; A61F 2210/009; A61F 2/013; A61F 2/82; A61F 2/95; A61J 17/003; A61J 17/006; A61J 17/007; A61L 9/015; A61L 9/20; A61M 2021/0044; A61M 21/02; A61M 37/00; A61N 2005/005; A61N 2005/0626; A61N 2005/0644; A61N 2005/0651; A61N 2005/0659; A61N 2005/0663; A61N 2005/1011; A61N 5/0616; A61N 5/0618; A61N 5/0619; A61N 5/062; A61N 5/0622; A61N 7/00; A62B 17/006; A62B 17/04; A62B 23/00; B01D 2251/104; B01D 2253/102; B01D 2257/504; B01D 2257/91; B01D 2259/4541; B01D 2259/4558; B01D 2259/4566; B01D 2259/4583; B01D 2259/804; B01D 53/38; B01D 53/86; B60J 10/00; C01B 13/10; C01B 13/11; C01B 2201/82; G01F 23/0076; G01F 23/20; G01F 23/263; G01F 23/2962; G01F 23/36; G02B 2027/014; G02B 2027/0187; G02B 27/01; G16H 40/67; Y02A 90/26
USPC ..... 340/632, 636.11, 636.1, 675, 680, 686.4, 340/686.6, 691.6, 693.2, 693.4
See application file for complete search history.

(56) References Cited

U.S. PATENT DOCUMENTS

| | | | |
|---|---|---|---|
| 2014/0163664 A1* | 6/2014 | Goldsmith | A61B 17/00491 623/1.11 |
| 2015/0094914 A1* | 4/2015 | Abreu | B60H 1/00742 701/41 |
| 2017/0304147 A1* | 10/2017 | Glenn | A61H 31/02 |

* cited by examiner

Data Log

| Time | Date | Log In Out | Helmet user | User Channel | Helmet user Title | High Pressure Primary Air Supply | Primary Low Pressure Air Supply | High Pressure Secondary Air Supply | Secondary Low Pressure Air Supply | Air Module Operator | Environmental Data | Gas Content |
|---|---|---|---|---|---|---|---|---|---|---|---|---|
| 12:40:57 | 5/13/2019 | IN | John | Red | Supervisor | 2500 | 125 | 2500 | 123 | Pat | 75°F | H2S 10 ppm |
| 12:40:58 | 5/13/2019 | IN | Mary | Blue | Entrant | 2650 | 125 | 2400 | 123 | Pat | 75°F | H2S 10 ppm |
| 12:40:59 | 5/13/2019 | IN | Pete | Green | Safety | 2900 | 125 | 2300 | 123 | Pat | 75°F | H2S 10 ppm |
| 12:41:08 | 5/13/2019 | IN | Zach | Yellow | Inspector | 750 | 125 | 2500 | 123 | Pat | 75°F | H2S 10 ppm |
| 12:41:09 | 5/13/2019 | IN | James | Black | Mechanic | 3000 | 125 | 2400 | 123 | Pat | 75°F | H2S 10 ppm |
| 12:41:10 | 5/13/2019 | IN | William | White | Welder | 600 | 125 | 2300 | 123 | Pat | 75°F | H2S 10 ppm |
| 12:41:11 | 5/13/2019 | IN | Robert | SAR 1 | Cleaner | 1495 | 125 | 0 | 0 | Pat | 75°F | H2S 10 ppm |
| 12:41:12 | 5/13/2019 | IN | Glenn | SAR 2 | Rescue | 1650 | 125 | 0 | 0 | Pat | 75°F | H2S 10 ppm |
| 12:41:13 | 5/13/2019 | IN | Chirs | SAR 3 | Worker | 2540 | 125 | 0 | 0 | Pat | 75°F | H2S 10 ppm |
| 12:41:14 | 5/13/2019 | IN | Evan | SAR 4 | Operator | 1540 | 125 | 0 | 0 | Pat | 75°F | H2S 10 ppm |
| 12:41:15 | 5/13/2019 | IN | Bobby | SAR 5 | Instructor | 1300 | 125 | 0 | 0 | Pat | 75°F | H2S 10 ppm |

Clear Data Table  Data Transfer

SYSTEM FOR AUTOMATICALLY REGULATING BREATHING AIR SUPPLY AND DATA LOGGING

CROSS REFERENCE TO RELATED APPLICATION

The present application claims priority to and the benefit of U.S. Provisional Patent Application Ser. No. 62/721,161, filed Aug. 22, 2018 and titled "System for Automatically Regulating Breathing Air Supply and Data Logging." This reference is hereby incorporated in its entirety.

FIELD

The present embodiment generally relates to a wireless system to automatically monitor and regulate high pressure input breathing air supply and automatically supply low pressure air supply for confined spaces for a plurality of sealing and locking helmets and/or supplied air respirators simultaneously.

BACKGROUND

A need exists for an air breathing system usable for operators in closed spaces that is flexible with multiple alarms to multiple client devices.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The invention relates to a system and an automated robotic trailer for simultaneously supplying and regulating breathing air to a plurality of sealing and locking helmets simultaneously of a plurality of users. Embodiments include a system and an automated robotic trailer of supplying and regulating breathing air to a plurality of air respirators of a plurality of users.

Embodiments contemplate a system and an automated robotic trailer to supply and regulate breathing air to a plurality of users simultaneously, each user wearing either a sealing and locking helmet or an air respirator.

The system and the automated robotic trailer simultaneously produce a plurality of lower pressure air supplies each low pressure air supply for a plurality of users (people) simultaneously using an air module containing an air processor with computer instructions to automatically receive data from a plurality of pressure sensors and at least one temperature sensor in the sealing and locking helmets or air respirators and in the atmosphere surrounding the user proximate the sealing and locking helmet or air respirators, compare received data to preset limits, and provide commands to a plurality of air regulators, valves, in view of the compared data ensuring consistent breathing air flow to a user. Embodiments contemplate the invention can additionally monitor stress of users including heart rates, blood pressure, body temperature, and breathing frequencies and provide alarms to an operator when users exceed or fall below preset limits while the system simultaneously provides the low pressure breathing air to the sealing and locking helmets and/or air respirators.

The system includes a plurality of temperature sensors of measuring the temperature of the environment around each person of one of the sealing and locking helmets or supplied air respirators, a gas analyzer, an air module processor controlling valves, receiving data from the pressure sensors, controlling lower pressure air supply and presenting data on a display with real time updates that are presented in less than a few milliseconds providing a continuously imported status that achieves safe entry in a hazardous area with fewer accidents by operators, cleaning crew, inspectors, welders, installers, and loaders.

The term "administrative processor" refers to a device which receives data from pressure sensors, has outputs to turn valves on and off and collects the signals and information from the pressure sensors based on the program that is installed at a remote location.

The term "air module" refers to a device that contains the air regulators, valves and pressure sensors.

The term "air module memory" refers to a device which stores data and various computer instructions.

The term "air processor" refers to a device which receives data from pressure sensors, and temperature sensor, and has outputs to turn the plurality of valves on and off and collects the signals and information from the pressure and temperature sensors based on the program that is installed within the data storage connected to the processor of the air processor. In embodiment, the air processor connects to memory that can have a self-check self-calibration program to perform self-diagnostics to detect leaks or defects in the sensors and valves.

The term "air regulators" sometimes referred to as "regulators" refers to a device within the air module that changes the air pressure.

The term "air supply" refers to compressed breathing air source.

The term "alarm" refers to alerts stored in memory connected to the air processor that are outside of the defined parameters of the helmet module.

The term "alarm status viewer" refers to a section on the display that allows a user to view the alarms from the air module processor.

The term "client device" refers to a laptop, a cell phone, a desk top computer, programmable logic circuit, and combinations thereof, or any electronic device connected to the network and viewed by the user, or any combination thereof.

The term "data log" refers to the accumulation of stored information from all of the processors.

The term "display" refers to an electronic device generating a visual presentation of data.

The term "gas analyzer" refers to device that calculates and measures the content of specified gasses in the air and sends an electronic signal to the air processor which is then interprets the electronic signals into useable information. The gas analyzer is a device measuring gas contents inside or outside of the vessel.

The term "network" refers to a cellular, satellite, global communication network, local area network, wide area network, fiber optic network, or combinations thereof.

The term "power supply" can refer to batteries, a battery charger and bank of batteries, or a grid to a low voltage power.

The term "pressure sensor" refers to a device that calculates and measures the pressure of the air and sends an electronic signal to the air processor which is then interpreted as a pressure.

The term "pressurized breathing air" refers to compressed breathing air which has been regulated down to a useable pressure.

The term "RFID reader" refers to device used to gather information stored on RFID ("radio frequency identifier") cards.

The term "sealing and locking helmet" refers to device that seals onto a user's head and provides breathing air.

The term "set up module" refers to a set of computer instructions stored in the memory of the air processor which allows the authorized user to input and customize additional authorized users of the entire system.

The term "temperature sensor" refers to a device which sends an electronic signal to the air processor which is then interpreted as a temperature.

The term "test panel" refers to a device measuring flow and functionality of the sealing locking helmet.

The "test panel display" refers to an electronic device generating the visual presentation of the measurement of flow and functionality of the sealing locking helmet.

The term "user" can refer to a person wearing a sealing and locking helmet, or another air breathing subject wearing a sealing and locking helmet or supplied air respirator.

The term "valves" refers to a device that controls the passage of air by turning the flow of air on and off.

One of the benefits of this invention is that the system prevents casualties by monitoring and controlling the delivery of breathing air to many users simultaneously.

Another benefit of the system is that the system can continuously monitor the surrounding work environment to avoid user exposure to poisonous and explosive gasses and extreme temperatures.

Another benefit of the invention includes the ability of a user of the supplied air devices to control their own air supply, wherein an administrative processor allows a user of a helmet or air respirator to turn on or off their own air.

A benefit of the invention is the system data logs all past event information providing a historical record of air use and temperatures.

Still another benefit of the invention is that the system provides more consistent testing and safer field use of supplied air devices.

The system provides a significant benefit using multiple RFID readers to consistently track tested locking and sealing helmets to ensure safe operation of the helmets and improved traceability preventing accidents that cause casualties to workers.

The system monitors proper OSHA safety procedures and provides alarms to cell devices dynamically when specifications exceed or fall below preset limits.

The system has various checks to only allow qualified personnel with the correct access permissions to use the system, and control air on and off to multiple users simultaneously.

Note that not all embodiments will necessarily manifest all benefits and that different embodiments may manifest different benefits to different degrees.

Figure 1:
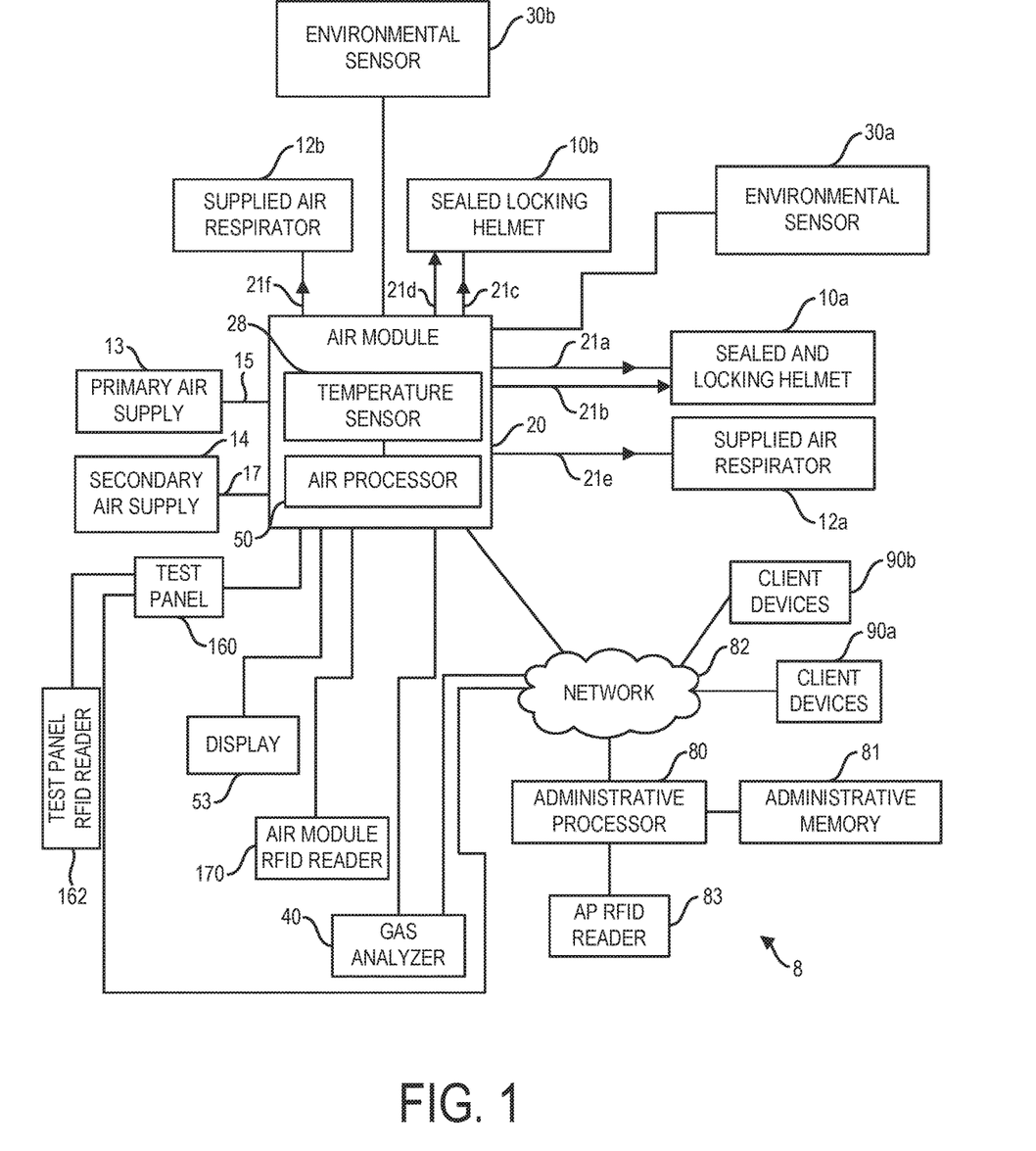
FIG. 1 depicts an overview of the air breathing system with connected sealing and locking helmets and a plurality of supplied air respirators for providing breathing air to users.

Turning now to the Figures, FIG. 1 depicts an overview of the air breathing system with a plurality of connected sealing and locking helmets and a plurality of supplied air respirators providing breathing air to a plurality of users, all simultaneously.

FIG. 1 shows the system 8 to regulate provide low pressure breathing air from a plurality of higher pressure air sources simultaneously to a plurality of sealing and locking helmets 10a and 10b and optionally or a plurality of supplied air respirators 12a and 12b.

Figure 2:
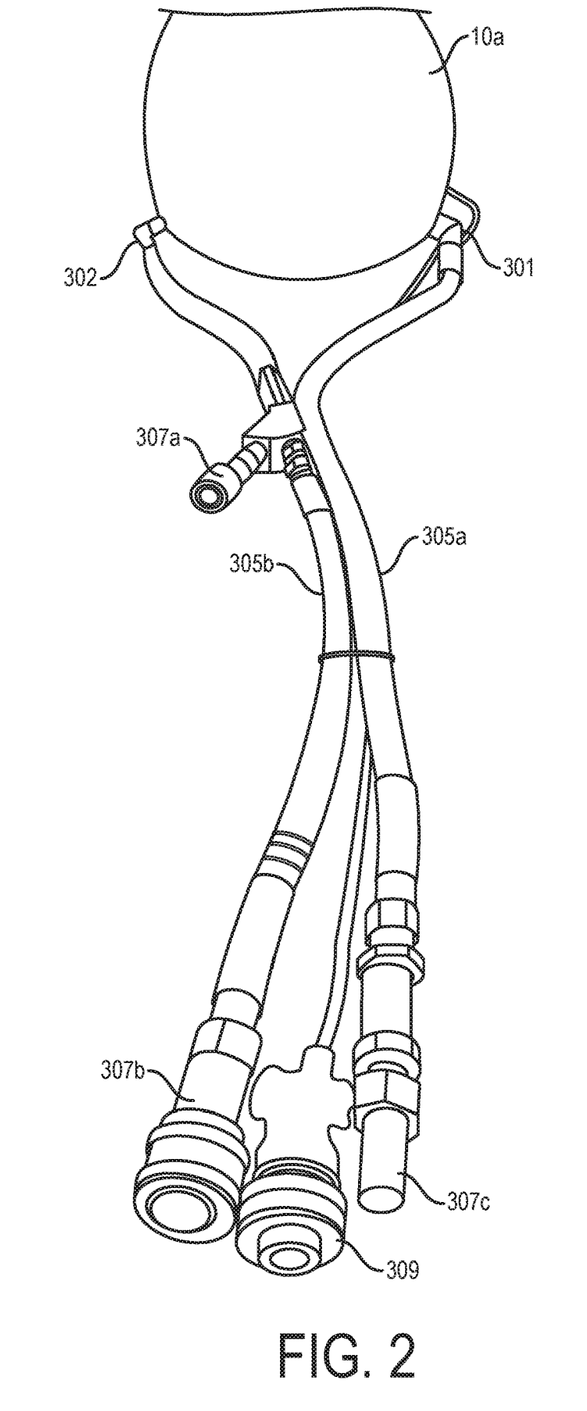
FIG. 2 depicts a detail of an exemplary sealing and locking helmet with attached hoses.

Each sealing and locking helmet has a low pressure primary air supply port 301 shown in FIG. 2 and a low pressure secondary air supply port 302 shown in FIG. 2 receiving the low pressure breathing air.

Returning to FIG. 1, each sealing and locking helmet, such as sealing and locking helmet 10a receives a low pressure primary air supply 21a and a low pressure secondary air supply 21b. The sealing and locking helmet 10b receives a low pressure primary air supply 21c and a low pressure secondary air supply 21d.

The primary and secondary low pressure air supplies are provided simultaneously to the sealing and locking helmets.

The low pressure air is supplied to each sealing and locking helmet via two supply hoses, 305a and 305b as depicted in FIG. 2.

Returning to FIG. 1, the system 8 also provides low pressure breathing air to a plurality of supplied air respirators 12a and 12b, respectively. Supplied air respirator 12a receives low pressure breathing air 21e and supplied air respirator 12b receives low pressure breathing air 21f.

The system 8 has a high pressure primary air supply 13. The high pressure primary air supply 13 can be one or more bottles of compressed air or a compressor.

The high pressure primary air supply 13 flows high pressure air 15 overr 200 psi to an air module 20.

The system 8 has a high pressure secondary air supply 14. The high pressure secondary air supply 14 can be one or more bottles of compressed air or an air compressor. The high pressure secondary air supply provides high pressure air simultaneously with the high pressure primary air supply 13 to the air module 20.

The high pressure secondary air supply 14 flows pressurized air supply 17 over 150-200 psi to the air module 20.

The air module 20 is fluidly and electronically connected to each of the plurality of sealing and locking helmets 10a and 10b, and if used, fluidly and electronically to each of the supplied air respirators 12a and 12b.

The air module 20 is configured to reduce high pressure primary and high pressure secondary air supplies simultaneously, or variably, depending on individual user need and produce a plurality of low pressure air supplies 2 la-f, less than 25 psi and as low as 2 psi, all simultaneously with pairs of low pressure air supplies going to each sealing and locking helmet.

Figure 3:
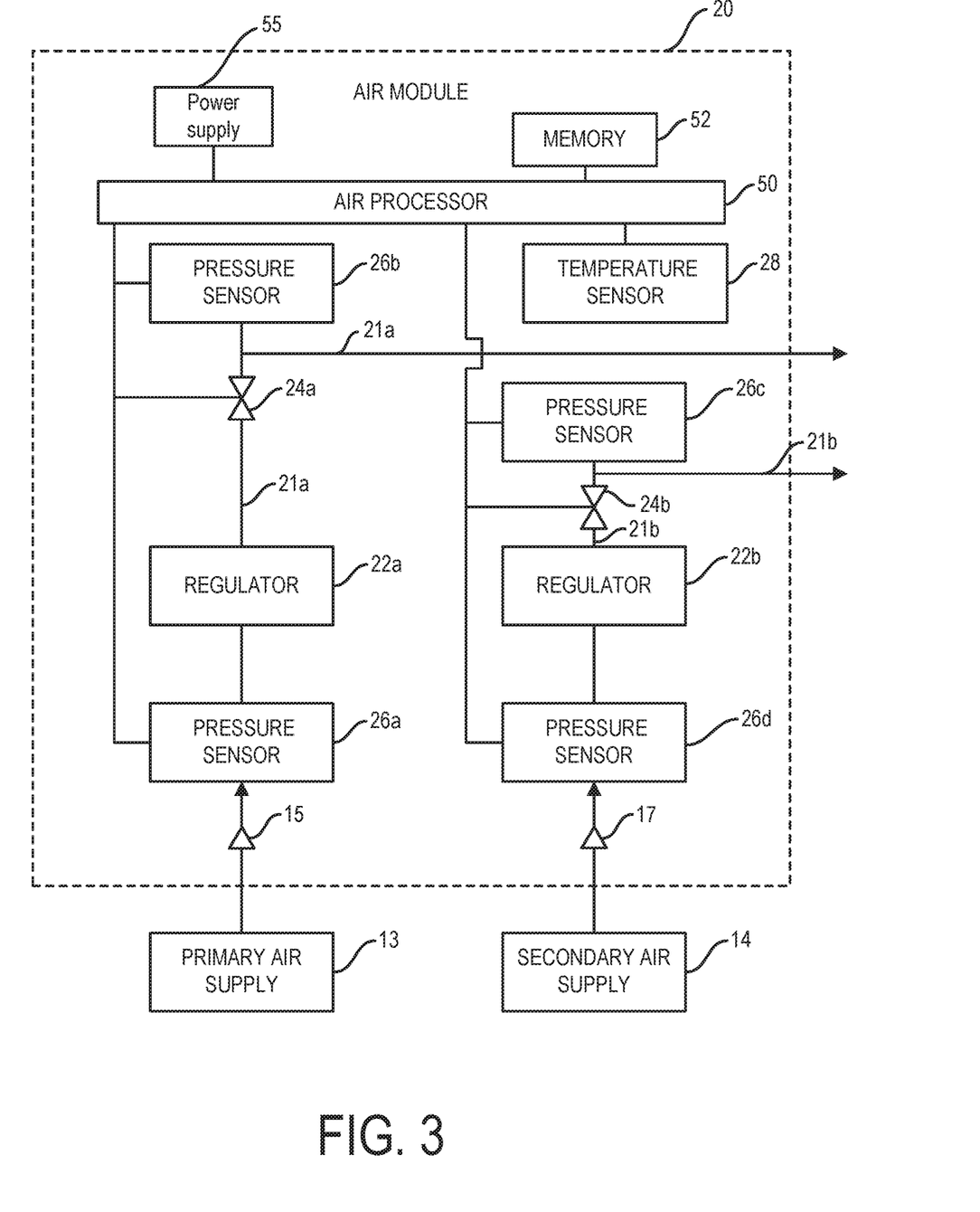
FIG. 3 depicts a detail of the air module of an embodiment.

The air module 20 is shown in more detail in FIG. 3.

In FIG. 1, the air module 20 is depicted with an air processor 50.

FIG. 3 shows the air processor 50 in the air module 20 electronically connected to memory 52.

Returning to FIG. 1, the air module 20 receives high pressure air 15 from the high pressure primary air supply 13 and then lowers the pressure to a breathing air pressure while simultaneously controlling air velocity and pressure then providing a plurality of streams of low pressure breathing air to the sealing and locking helmets shown in this figure as low pressure air supply 21a-d.

The air processor 50 electronically communicates with a plurality of components, including a test panel 160 that additionally communicates with a network 82, either wirelessly or in a wired manner. The test panel is separate from the air module.

The test panel enables calibration of each sealing and locking helmet. The test panel provide set up of each sealing and locking helmet.

The air processor 50 also communicates electronically with a gas analyzer 40 that additionally can communicate directly with the network 82.

The air processor 50 can communicate with both an air module display 53 and an air module RFID reader 170 that can read sealing and locking helmet information.

The air module 20 has a temperature sensor 28 contained in the housing of the air module.

The air module 20 can communicate with a group of environmental sensors 30a and 30b. Each environmental sensor is external of the air module and proximate to each sealing and locking helmet or supplied air respirator such as within 1 or 2 feet of the user.

In this FIG. 1, two environmental sensors are shown one for each sealing and locking helmet and identified as elements 30a and 30b.

In embodiments, the environmental sensors can communicate electronically with the network and the air module.

The air module RFID reader 170 is electronically connected to the air processor 50 and is configured to verify that a user has permission to adjust valve settings of one of the sealing and locking helmets, set alarm points of temperature, pressure and gas content within or surrounding each sealing and locking helmet, and/or supplied air respirator, and set limits of specific gasses that are being detected by the gas analyzer and add new user data and user profiles of each sealing and locking helmet.

In embodiments, the air module RFID reader 170 can be used to scan codes to add new user data and user profiles into memory connected to the air processor of each sealing and locking helmet.

The memory can contain a "helmet module" of individual users and a plurality of users simultaneously allowing preset limits by individual, by environment each individual is in, and by type of gases in the environment.

The test panel 160 is electronically connected to the air module 20. In embodiments the test panel has a separate test panel display in communication with a test panel RFID reader 162. RFID stands for radio frequency identification. Details of the test panel 160 as connected to a sealing and locking helmet are further depicted in FIG. 7.

The test panel can import RFID scanned data using the test panel RIFD reader and verify an identity of a user. The test panel RIFD reader 162 can import user specific or environment specific characteristics and specifications concerning each user.

Specifically the test panel RFID reader communicates with a test panel memory with computer instructions instructing a test panel processor to match imported data to: (i) enable identification of each sealing and locking helmet or identification of each sealing air respirator, and (ii) enable identification of a specific user.

Inside the air module shown in FIG. 1 is an air module temperature sensor 28 to detect and measure temperatures inside the air module 20 and electronically connected to the air processor 50 providing measured temperature conditions to the air processor to compare the temperatures to preset limits in memory using the "helmet module."

The environmental sensors 30a and 30b shown in FIG. 1 are electronically connected to the air processor 50 in the air module 20, and are configured to detect temperatures, air pressures, gas content, or combinations thereof.

Each environmental sensor is located proximate each sealing and locking helmet and external to each sealing and locking helmet and each supplied air respirator and is configured to transmit detected temperatures, pressures and gas contents, to the air processor 50 and memory generating comparison to user specifications in the "helmet module", discussed further below, in the memory and preset limits in the "helmet module" in memory.

A gas analyzer 40 is electronically connected to the air module 20 and optionally to the network 82. The gas analyzer is sampling, and analyzing gas components in the environment around, and external to, each sealing and locking helmet, and optionally external to each supplied air respirator.

The air processor 50 wirelessly or in a wired manner electronically connects with the network 82 that further connects to a plurality of client devices, 90a and 90b and to an optional administrative processor 80. The processors can be computers.

The administrative processor 80 electronically connects to an administrative memory 81 and to an administrative processor RFID reader 83.

The administrative processor (AP) RFID reader 83 can be used to read administrator information and verify whether a user can enter new user profiles, or set gas limits or temperature limits into the helmet module of the memory of each air module or a plurality of air modules simultaneously.

The client devices of FIG. 1 can be a cell phone and a tablet computer, a wearable computer, or a plurality of cell phones.

The administrative processor can be a cloud based processor.

The AP RFID reader 83 enables a plurality of administrative users to each have different permissions and different access controls to specifications and data of the system and the helmet module.

The system 8 operates continuously importing data 24 hours a day, 7 days a week to achieve safe entry in a hazardous area for workers and thereby reduce accidents by operators, cleaning crew, inspectors, welders, installers, and loaders.

FIG. 2 depicts a detail of an exemplary sealing and locking helmet 10a with attached supply hoses 305a and 305b.

The sealing and locking helmet 10a has a low pressure primary air supply port 301 receiving a low pressure primary air supply through supply hose 305a and a low pressure secondary air supply port 302 receiving a low pressure secondary air supply through supply hose 305b, all simultaneously. Each hose connects to the air module 20.

The sealing and locking helmet 10a has a plurality of air supply fittings 307a,b, and 307c to couple the air supply hoses to the air module or the sealing and locking helmet enabling quick connect and disconnect fast install and use in emergency situations.

The sealing and locking helmet 10a has a communication cable 309 providing at least one of audio communication and video communication from the air module 20 to the sealing locking helmet 10a or vice versa. The sealing and locking helmet can have a visual display interior of the helmet (not shown) providing video feed to the wearer or alternatively a connection to a camera on the helmet, allowing video feed from the sealing and locking helmet to the air module and ultimately the administrative processor and client devices monitoring the system.

FIG. 3 depicts an air module 20 of the system receiving two streams of pressurized breathing air 15 and 17. The pressurized high pressure air 15 comes from the high pressure primary air supply 13. The pressurized high pressure air 17 comes from the high pressure secondary air supply 14.

For this FIG. 3, the air module 20 is configured to receive high pressure air at 3000 psi.

The air module 20 detects the incoming pressure using pressure sensors 26a and 26d and transmits the data to the air processor 50 which is powered by a power supply 55.

Figure 4:
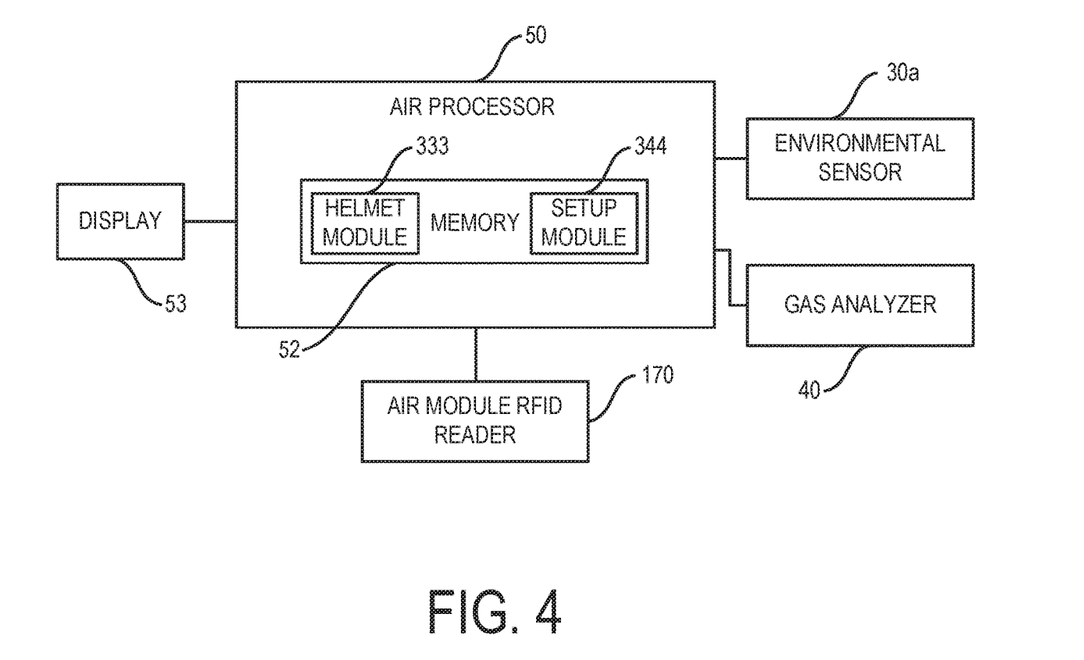
FIG. 4 depicts an air processor usable in an embodiment.

The air processor 50 uses computer instructions in the memory 52 shown in FIG. 3 to compare the detected pressure to preset limits using the helmet module 333 shown in FIG. 4 in the memory and then transmitting a command to one or more of the air regulators 22a and 22b and valves 24a and 24b to open a preset amount to thereby reduce or increase quantities of high pressure air flowing to the valves or regulators.

The air coming from the regulators are from low pressure air supplies 21a and 21b.

Additional pressure sensors 26b and 26c detect the lowered pressure and transmit the detected lowered pressure to the air processor 50.

For this FIG. 3, each pair of lowered pressure air supplies transfers to one of the plurality of sealing and locking helmets or to one of the plurality of supplied air respirators.

The plurality of air regulators 22a, and 22b are configured to convert the high pressure primary air supply stream 15 and high pressure secondary air supply stream 17 to the low pressure air supply 21ab simultaneously. In this embodiment, the plurality of air regulators are connected in parallel to each other.

Each air regulator 22a and 22b steps down the pressurized breathing air to a lower pressurized air supply.

The plurality of valves 24ab, are each configured to receive the low pressure air supply from one of the regulators and control low pressure air flow to one of the ports on one of the sealing and locking helmets.

Each valve is also electronically connected to the air processor 50.

Each valve is configured to turn the lower pressure supply on or off.

In embodiments, the quantity of valves are in a 4:2 to 1:1 ratio to the total number of supplied air respirators and sealing and locking helmets used in the system.

The plurality of pressure sensors 26abc are configured so that one of the pressure sensors measures air pressure of one of the low pressure air supplies, and each high pressure primary air supply and each high pressure secondary air supply.

Pressure sensors 26a and 26d are configured to measure air pressure of each high pressure air supply entering the air module and prior to modification of the pressure by one of the air regulators.

Pressure sensors 26b and 26c are configured to measure air pressure of each low pressure air supply 21a and 21b coming from the air regulators 22a and 22b respectively.

The air module includes a temperature sensor 28 electronically connected to the air processor 50 to measure temperature in the air module and transmit the temperature to the air processor of the helmet module in memory.

FIG. 4 depicts a detail of an air processor 50 of the system.

The air processor 50 is electronically connected to an environmental sensor 30a measuring temperature of environment around one of the sealing and locking helmets or one of the supplied air respirators.

FIG. 4 also shows a gas analyzer 40 electronically connected to the air processor 50.

The gas analyzer is analyzing gas in the environment around one of the sealing and locking helmets or around one of the supplied air respirators.

FIG. 4 shows the air processor 50 having memory 52.

The air processor 50 is shown electronically connected to the air module display 53.

The memory 52 is shown having a helmet module 333.

The memory 52 can include a setup module 344.

The setup module 344 can include computer instructions to automatically create and display personnel profiles on the display, computer instructions to automatically display status of a lock out timer, computer instructions to automatically display user data tables with individual permissions of each user, and computer instructions instructing the processor to add or delete users.

FIG. 4 shows air module RFID reader 170 electronically connected to the air processor 50.

The air module RFID reader 170 is used to scan RFID data secured to the sealing and locking helmets or the supplied air respirators.

The air module RFID reader 170 is used to verify that a particular user has permission to adjust valve settings of an individual sealing and locking helmet and permission to adjust valve settings of a specific supplied air respirator.

The air module RFID reader provides data enabling a user with certain permissions to set alarm points of temperature and gas type and concentration and to add new user data and new user profiles to the system 8.

Figure 5A:
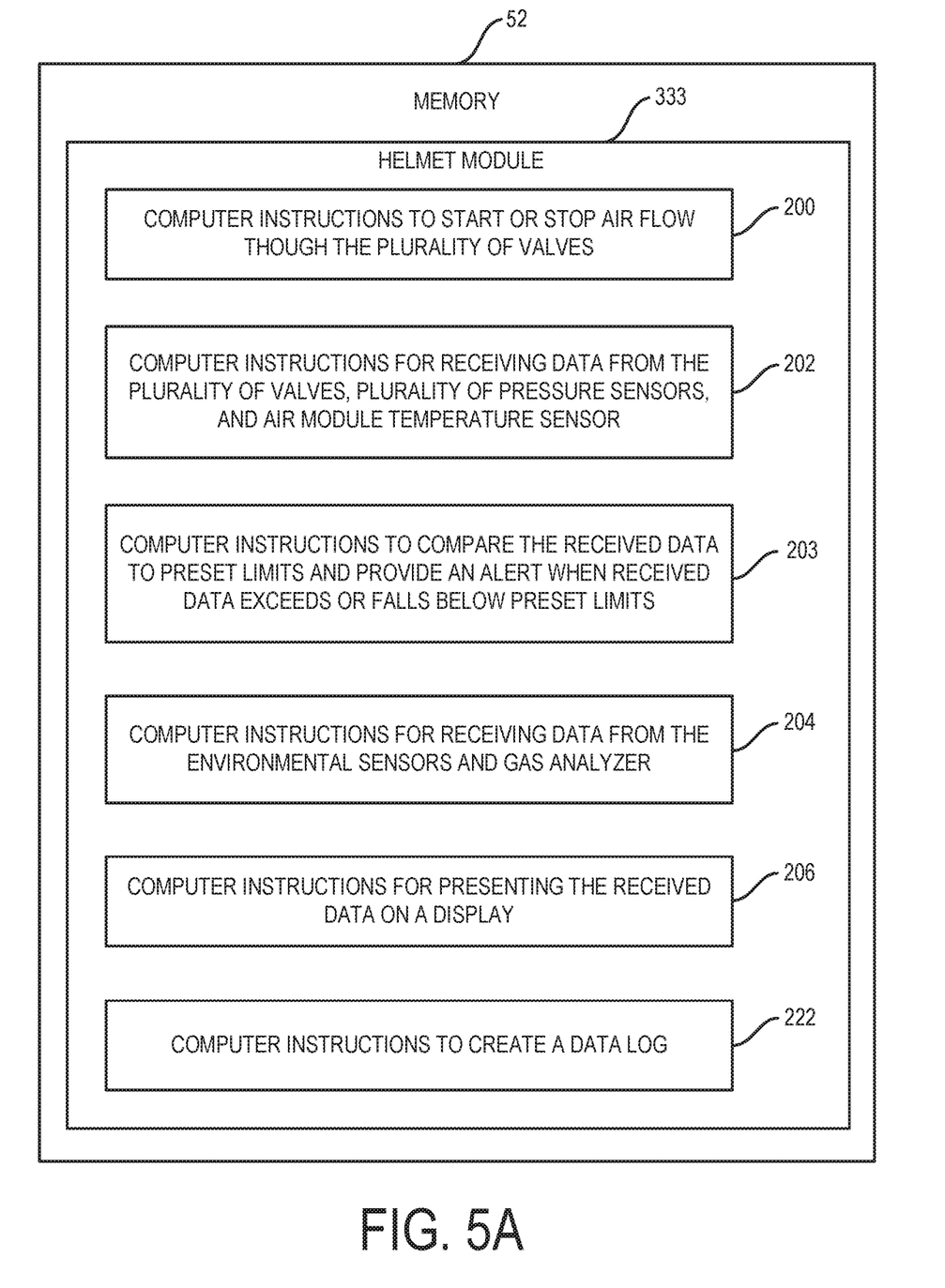
FIGS. 5A-5B depict a memory with a helmet module according to an embodiment.
Figure 5B:
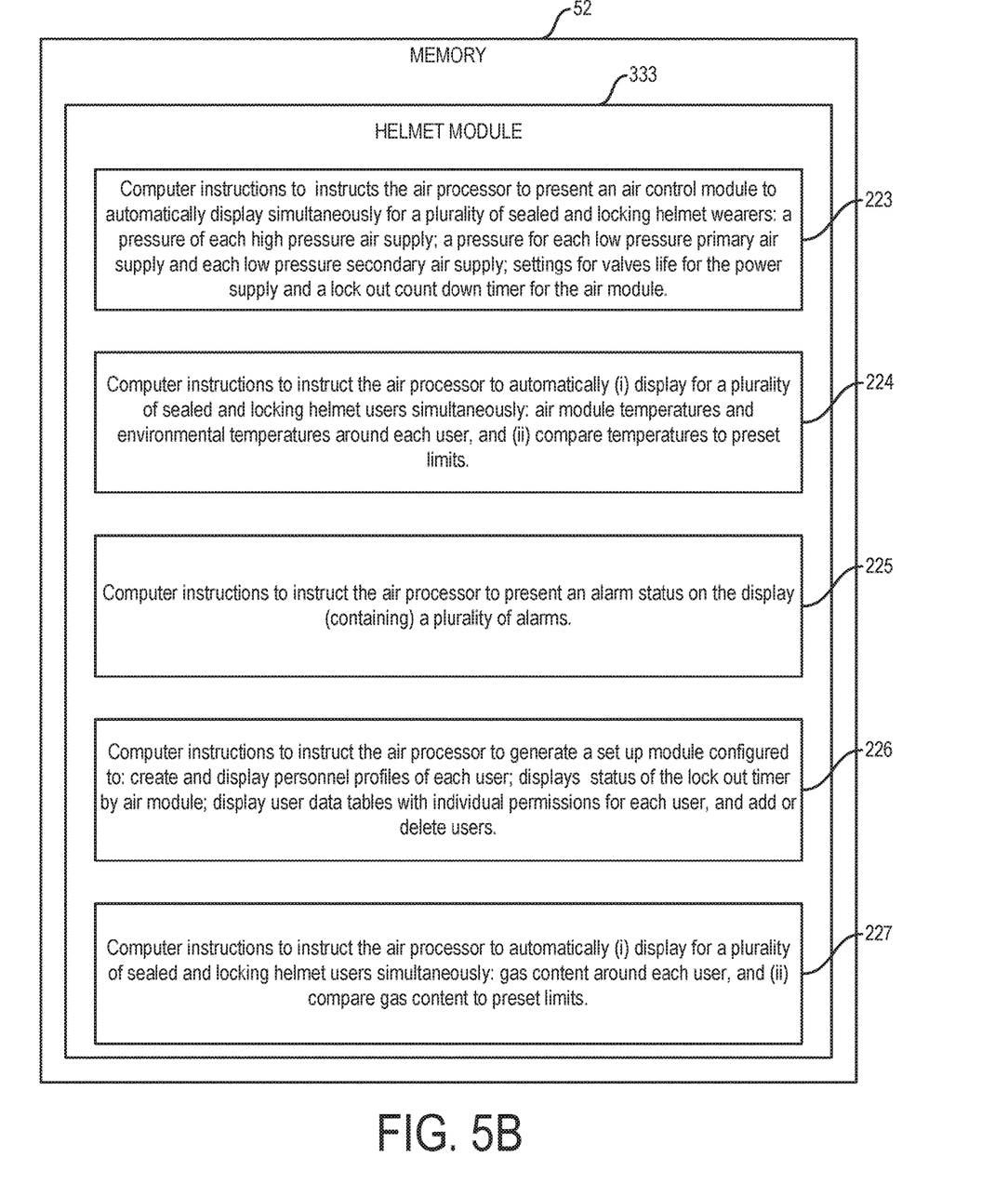

FIG. 5A-5B depicts the memory 52 of the air module 20.

The memory 52 includes the helmet module 333 represented by the solid line around a plurality of computer instructions.

The helmet module 333 includes computer instructions 200 to instruct the air processor to start or stop air flow through the plurality of valves. In embodiments, the computer instructions 200 can start air flow through only one valve.

The helmet module 333 includes computer instructions 202 to instruct the air processor to receive data from the plurality of valves, plurality of pressure sensors, and the air module temperature sensor.

The helmet module 333 includes computer instructions 203 to instruct the air processor to compare the received data to preset limits and provide an alert when received data exceeds or falls below preset limits.

The helmet module 333 includes computer instructions 204 to instruct the air processor to receive data from the environmental sensors and gas analyzer.

The helmet module 333 includes computer instructions 206 to instruct the air processor to present the received data on a display.

The assembled system provides continuous monitoring and continuous provision of reliable low pressure breathing air of a user while being protected from breathing undesired components in a hazardous environment.

The helmet module 333 includes computer instructions 222 to instruct the air processor to generate a data log 310 automatically.

Figure 6:
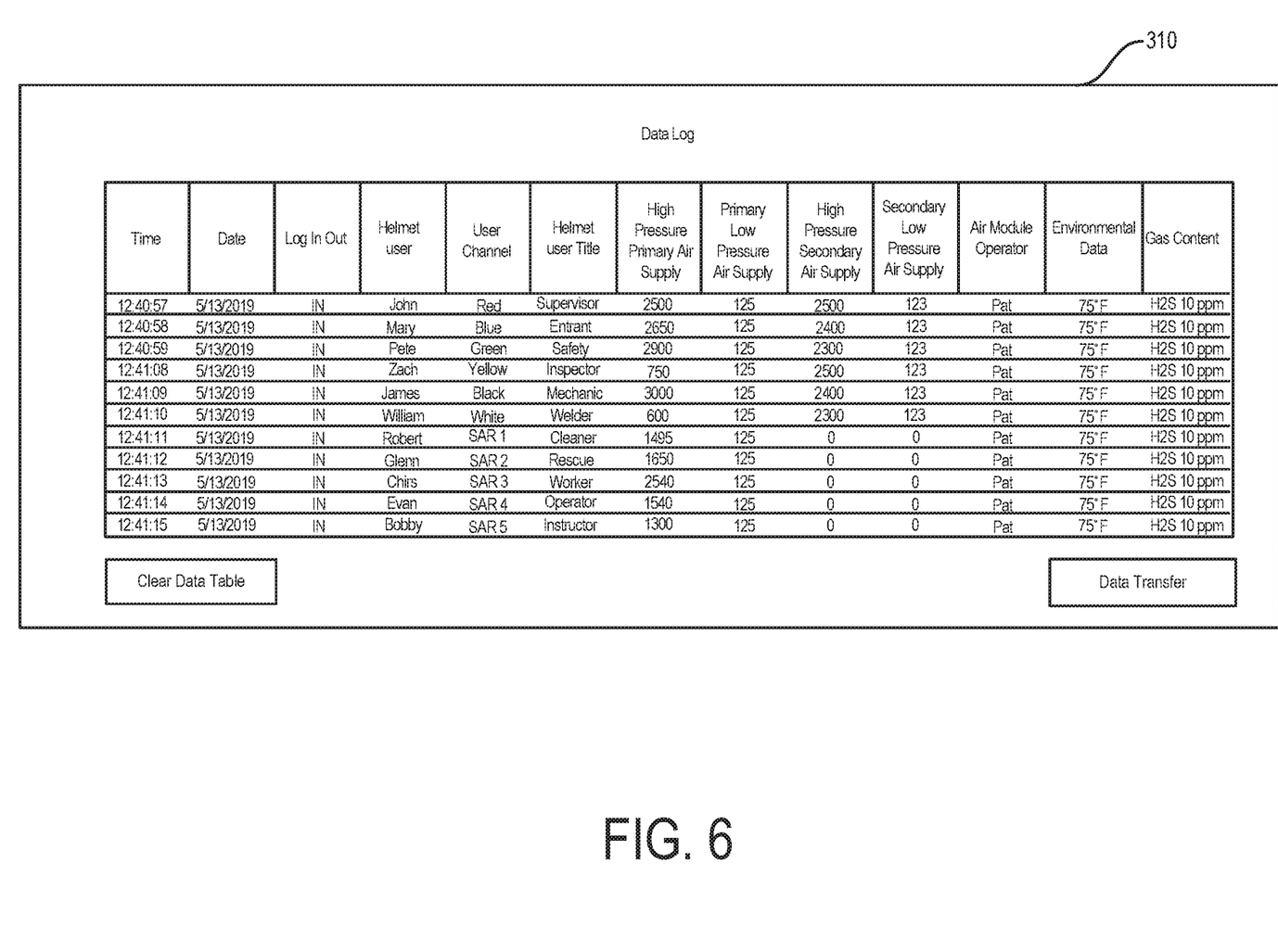
FIG. 6 depicts an exemplary data log according to an embodiment.

FIG. 6 shows the data log 310 can include all or a portion of the following data: Time; Date; Log In Out; Helmet user; user channel, helmet user title; High pressure primary air supply; low pressure primary air supply; high pressure secondary air supply; low pressure secondary air supply; air module operator, environmental data; and gas content.

Returning to FIG. 5B, the helmet module 333 includes computer instructions 223 to instructs the air processor to present an air control module to automatically display simultaneously of a plurality of sealing and locking helmet wearers: a pressure of each high pressure air supply; a pressure of each low pressure primary air supply and each low pressure secondary air supply; settings of the valves; remaining life of the power supply; and a lock out count down timer of the air module.

The helmet module 333 includes computer instructions 224 to instruct the air processor to automatically (i) display of a plurality of sealing and locking helmet users simultaneously: air module temperatures and environmental temperatures around each user, and (ii) compare temperatures to preset limits.

The helmet module includes computer instructions 225 to instruct the air processor to present an alarm status on the display containing a plurality of alarms.

The alarms include: an "air does not match" alarm indicates the two air supply pressures to one of the helmets do not match each other; a low pressure air supply alarm indicating at least one of: the high pressure primary air supply and the high pressure secondary air supply falls below preset limits; a person appears not breathing alarm; a battery life of the air module has fallen below preset limits alarm; and an air module temperature exceeds a preset operating limit alarm.

The helmet module includes computer instructions 226 to instruct the air processor to generate a set up module configured to: create and display personnel profiles of each user; displays status of the lock out timer by air module; display user data tables with individual permissions of each user, and add or delete users.

The helmet module includes computer instructions 227 to instruct the air processor to automatically (i) display of a plurality of sealing and locking helmet users simultaneously: gas content around each user, and (ii) compare gas content to preset limits.

FIG. 6 depicts an exemplary data log 310 according to an embodiment.

The data log 310 comprising: Time; Date; Log In Out; Helmet user; Helmet user title; High pressure primary air supply; Low pressure primary air supply; High pressure secondary air supply; Low pressure secondary air supply; Environmental data; Gas content; and Air module operator.

The data log 310 shows time that data was collected.

The data log shows a date when data was collected.

The data log shows when a helmet is in use or out of use. "IN" means a user has acquired the sealing and locking helmet or the supplied air respirator.

The data log shows a helmet user name, such Pete.

The data log shows a helmet user title," which is a worker title such as "supervisor" in this FIG. 6.

The data log 310 shows a user channel which can be a colored air supply channel or a labelled channel with a number such as SAR 1, 2, 3, 4, 5, or 6.

The data log 310 has a high pressure primary air supply of individual helmet users, such as 2500 psi, or 2650 psi as shown in this FIG. 6.

The data log 310 has a low pressure primary air supply of individual helmet users, such as 125 psi.

The data log 310 has a high pressure secondary air supply of individual helmet users, such as 2500 psi or 2300 psi as shown in this FIG. 6.

The data log 310 has a low pressure secondary air supply of individual helmet users, such as 123 psi.

The data log 310 depicts of each helmet user, an air module operator shown as Pat in this FIG. 6.

The data log 310 depicts environmental data which of this FIG. 6 is showing temperature at 75 degrees Fahrenheit detected around each helmet user.

The data log 310 shows gas content. In this FIG. the gas being detected is hydrogen sulfide ($H_2S$) at 10 ppm.

The data log can depict a data transfer "button" enabling a user to set of automatically transfer data to another source.

The data log can record alarms by displaying a single alarm bell that can be green or red if a system has any alarms at all.

If an administrative processor is used connected to the network, then the data log can include an alarm status viewer containing several alarms.

The alarm status viewer can transmit a plurality of stored alarms to client devices via the network.

The alarms can include an "air does not match alarm" that indicates the two air supply pressures to one of the sealing and locking helmets do not match each other.

The alarms can include a "low pressure air supply pressure alarm" when low pressure supply pressure exceeds or falls below preset limits.

The alarms include a "person appears not breathing alarm".

The alarms include a "battery life alarm" indicating when power for the air module battery falls below preset limits.

The alarms include a "control equipment temperature alarm" of when control equipment temperatures exceed a preset operating limit.

The data log can be transmitted to one or all of the client devices connected to the network using a button the screen that activates optional computer instructions to automatically transmit stored data from pressure sensors and modules to a client device using the network.

The data log can include stored data from pressure sensors and temperature sensors which are directly presented to the display for viewing.

The data log can have a "button" titled "clear data table" that activates computer instructions to clear the data log.

Figure 7:
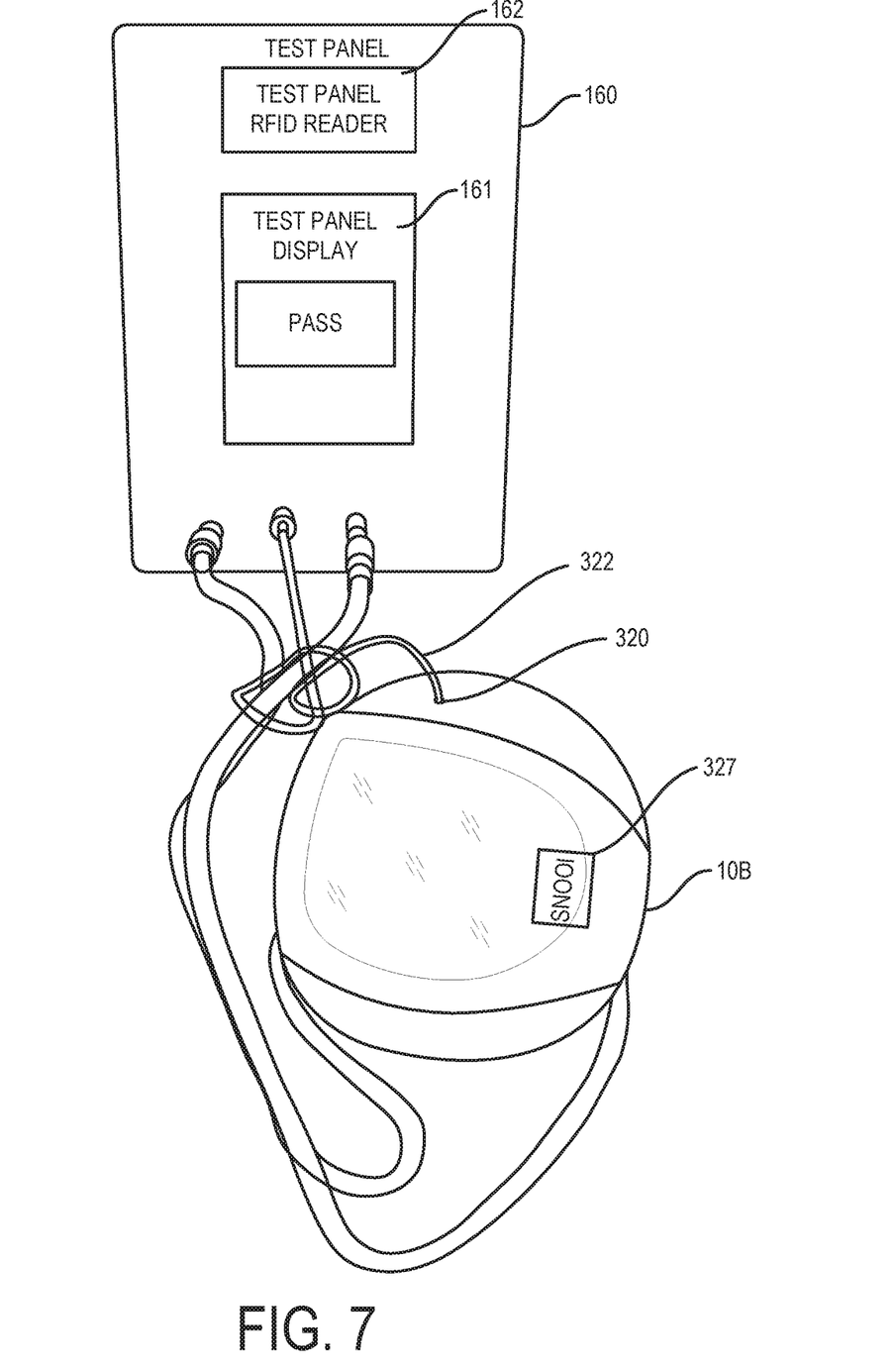
FIG. 7 shows a detail of the test panel connected to a sealing and locking helmet.
Figure 8:
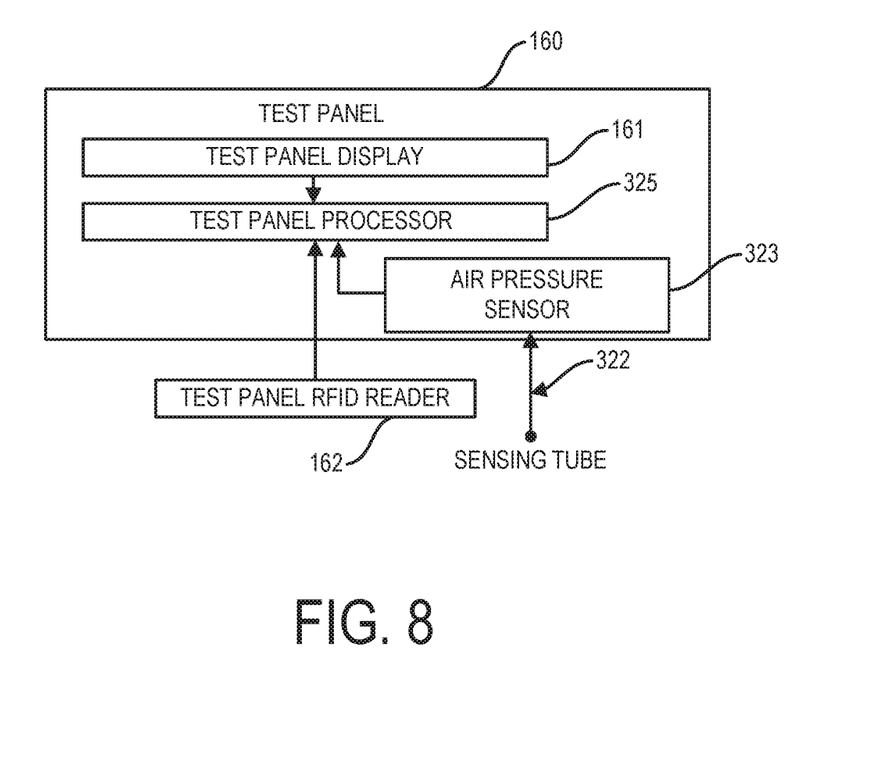
FIG. 8 is a diagram of components of an exemplary test panel.

FIG. 7 and FIG. 8 show details of the test panel 160 connected to a sealing and locking helmet 10b.

The test panel 160 engages the sealing and locking helmet through a sensing tube 322 connected to a sensing tube port 320 on the sealing and locking helmet.

The test panel has an air pressure sensor 323, (shown in FIG. 8) to detect air pressure inside each sealing and locking helmet via the sensing tube 322 and transmit the detected air pressure to a test panel processor 325 also shown in FIG. 8.

The test panel processor compares detected air pressure to preset limits, and further connects to a test panel RFID reader 162 that reads serial numbers 327 from each sealing and locking helmet and transmit the read serial number to the test panel processor to display test results associated with the serial number on a test panel display 161. The test panel display shows a pass or fail indicator, in FIG. 7 it shows "PASS".

The test panel RIF reader 162 is configured to read serial numbers 327, such as "SN001" as shown in FIG. 7, from each sealing and locking helmet or supplied air respirator and transmit the read serial number to the test panel processor 325 (shown in FIG. 8).

When air supplies via hoses from the sealing and locking helmet are connected to the test panel, the Test Panel RFID Reader can read the serial number from the helmet. The air pressure is compared to preset limits matching that sealing and locking helmet and a pass alert is generated when the air pressure falls within the pass limit.

The helmet can be tested separately via the test panel without using the air module.

In embodiments, the test panel and the air module processor are connected through a wired or wireless network.

In embodiments, the network is cellular, radio, satellite, global communication network, local area network, wide area network, fiber optic network, or combinations thereof.

In embodiments, the client device can be a laptop, a cell phone, a desk top computer, programmable logic circuit, and combinations thereof.

Example of the System

In an embodiment, the system to regulate breathing air can use 120 sealing and locking helmets and no supplied air respirators.

An air supply that is 120 bottles of compressed breathing air, each bottle having a pressure of 3000 psi is used.

The air module of the invention receives all 120 streams of compressed breathing air from the air supply.

The air module may include 120 air regulators, each receiving the pressurized breathing air and step down the pressurized breathing air to a lower pressurized supply of at least 125 psi for all 120 people.

The air module may include 240 valves that can be used to turn on and off the lower pressure supply air supply streams The quantity of valves of this example are in a 2:1 ratio to the sealing and locking helmets.

Three pressure sensors can be used per sealing and locking helmet, one on the air supply, and one on each primary and secondary breathing air supply to each sealing and locking helmet.

Each pressure sensor is electronically connected to an air module processor such as cloud based connected servers.

A first group of pressure sensors measures air pressure of each pressurized breathing air supply prior to each air regulator and a second group of pressure sensors measures air pressure of the lower pressure air supply and all the pressure sensors transmit their data to the cloud based system through a network.

A temperature sensor such as a Type K thermocouple probe made by Edelhoff Technologies, USA of Houston, Tex. is electronically connected to the air module processor. The temperature sensor configured to measure temperature in the air module and present the data on a display for operators to view.

Two environmental sensors per area of use are electronically connected to the air module measuring temperature of environment around groups of thirty sealing and locking helmets.

Four gas analyzers are connected to the air module, one gas analyzer is detecting and analyzing gas component in the environment around each groups of thirty sealing and locking helmets and transmitting the gas analysis data to the air module processor for display.

The air module processor is electronically connected to an air module cloud based memory and a display which can be a touch screen display. The air module memory includes computer instructions controlling all valves in the air module, computer instructions for receiving data from all the pressure sensors in the air module, computer instructions to control lower pressure air supply to each sealing and locking helmet, and computer instructions presenting the received data on the display with real time updates that are presented in less than two milliseconds.

While these embodiments have been described with emphasis on the embodiments, it should be understood that within the scope of the appended claims, the embodiments might be practiced other than as specifically described herein.

What is claimed is:

1. A system to regulate low pressure breathing air from a plurality of higher pressure air sources simultaneously to a plurality of sealing and locking helmets; the system comprising:
 a plurality of sealing and locking helmets, each sealing and locking helmet with a low pressure primary air supply port receiving a primary low pressure air supply and the sealing and locking helmet has a low pressure secondary air supply port 302 receiving a low pressure secondary air supply simultaneously;
 a plurality of pairs of air supply hoses, with one air supply hose of each pair connected to the low pressure secondary air supply port of a respective one of the sealing and locking helmets and another air supply hose of each pair connected to the low pressure primary air supply port of the respective one of the sealing and locking helmets;
 a plurality of environmental sensors measuring at least one of: temperature, gas content and pressure, of a hazardous environment around at least one of the sealing and locking helmets;
 a gas analyzer detecting and analyzing gas content in each environment around each sealing and locking helmet;
 an air module display to present data;
 an air module fluidly connected to a high pressure primary air supply, and a high pressure secondary air supply and fluidly connected to each of the plurality of sealing and locking helmets and electronically connected to the plurality of environmental sensors, the gas analyzer and the air module display; the air module configured to reduce the high pressure primary air supply and the high pressure secondary air supply and generate a plurality of low pressure primary air supplies and a plurality of low pressure secondary air supplies; the air module comprising:
 i. a plurality of air regulators converting a high pressure primary air supply and a high pressure secondary air supply to the low pressure air supplies, wherein the plurality of air regulators are connected in parallel to each other;
 ii. a plurality of pressure sensors, each pressure sensor configured to measure air pressure of each in-coming high pressure primary air supply and each in-coming high pressure secondary air supply and each generated low pressure air supply;
 iii. an air processor with memory and a power supply connected to the air processor, the memory containing a helmet module, the helmet module comprising:

(a) computer instructions to instruct the air processor to receive data from the plurality of pressure sensors, environmental sensors and gas analyzer;

(b) computer instructions to instruct the air processor to compare the received data to preset limits and provide an alert when received data exceeds or falls below preset limits;

(c) computer instructions to instruct the air processor to present the received data on air module display; and wherein the system provides continuous monitoring and continuous provision of reliable breathing air multiple users while protecting the multiple users from breathing undesired gas content in the hazardous environment.

2. The system of claim 1, further comprising: a plurality of valves, each valve configured to receive the low pressure air supply from one of the air regulators and control low pressure air flow to one of the sealing and locking helmets and wherein the helmet module comprises: computer instructions to instruct the air processor to start or stop air flow through the plurality of valves and computer instructions to instruct the air processor to receive data from the plurality of valves.

3. The system of claim 2, wherein helmet module includes computer instructions to instruct the air processor to automatically display simultaneously a plurality of sealing and locking helmet users: a pressure of each high pressure air supply; a pressure of each low pressure primary air supply and each low pressure secondary air supply; settings of valves; remaining life of the power supply; and a lock out count down timer of the air module.

4. The system of claim 1, further comprising an air module temperature sensor in the air module to measure temperature in the air module and wherein in the helmet module comprises: computer instructions to instruct the air processor to receive data from the air module temperature sensor, compare received data to preset limits and provide an alarm when the temperature exceeds or falls below preset limits.

5. The system of claim 4, further comprising in the helmet module: computer instructions to instruct the air processor to generate a set up module configured to: create and display personnel profiles of each user; displays status of the lock out timer by air module; display user data tables with individual permissions of each user, and add or delete users.

6. The system of claim 4, comprising in the helmet module: computer instructions to instruct the air processor to automatically (i) display of a plurality of sealing and locking helmet users simultaneously: gas content around each user, and (ii) compare gas content to preset limits.

7. The system of claim 4, further comprising an air module RFID reader electronically connected to the air module enabling the air processor to verify that a user has permission to adjust valve settings of one of the sealing and locking helmets and set alarm points of temperature, pressure and gas content within or surrounding the sealing and locking helmet; and add new user data and user profiles of each sealing and locking helmet.

8. The system of claim 1, further comprising an administrative processor with administrative memory, and an administrative processor RFID reader to control access to user information, the administrative processor electronically connected o a network to communicate with the air module and a plurality of client devices connected to the network, to allow remote control, monitoring of data and storage of data from a plurality of air modules, simultaneously.

9. The system of claim 1, further comprising in the helmet module: computer instructions to instruct the air processor to generate a data log automatically, the data log comprising:
   a. Time;
   b. Date;
   c. Log In Out;
   d. Helmet user;
   e. Helmet user title;
   f. High pressure primary air supply;
   g. Low pressure primary air supply;
   h. High pressure secondary air supply;
   i. Low pressure secondary air supply;
   j. Air module operator;
   k. Environmental data; and
   l. Gas content.

10. The system of claim 1, further comprising in the helmet module: computer instructions to instructs the air processor to automatically (i) display of a plurality of sealing and locking helmet users simultaneously: air module temperatures and environmental temperatures around each user, and (ii) compare temperatures to preset limits.

11. The system of claim 1, further comprising in the helmet module: computer instructions to instruct the air processor to present an alarm status viewer on the display containing a plurality of alarms, the plurality of alarms comprising: an "air does not match" alarm indicating that the pressures of a respective low pressure primary air supply and a respective low pressure secondary air supply one of the sealing and locking helmets do not match; a low pressure air supply alarm indicating at least one of: the high pressure primary air supply pressure and the high pressure secondary air supply pressure has fallen below preset limits; a person appears not breathing alarm; a power supply life alarm; and an air module temperature exceeds a preset operating limit alarm.

12. The system of claim 1, further comprising a test panel that engages the sealing and locking helmet through a sensing tube connected to a sensing tube port on the helmet, the test panel having an air pressure sensor, to detect air pressure inside each sealing and locking helmet via the sensing tube and transmit the detected air pressure to a test panel processor, the test panel processor compares detected air pressure to preset limits, and further connects to a test panel RFID reader that reads serial numbers from each sealing and locking helmet and transmit the read serial number to the test panel processor to display test results associated with the serial number on a test panel display.

13. The system of claim 12, wherein the test panel is connected to a plurality of client devices and the air module through a wired or wireless network.

14. The system of claim 1, wherein the network is cellular, satellite, global communication network, radio network, local area network, wide area network, fiber optic network, or combinations thereof.

15. The system of claim 1, wherein the plurality of client devices is at least two of: a laptop, a cell phone, a desk top computer, programmable logic circuit, and combinations thereof.

16. The system of claim 1, further comprising, a plurality of supplied air respirators connected to the air module, each supplied air respirator receiving one of the low pressure primary air supplies and one of the low pressure secondary air supplies from the air module.

17. The system of claim 1, further comprising a plurality of air supply fittings to couple the air supply hoses to the air module providing quick connect and disconnect.

18. The system of claim 1, further comprising a communication cable providing at least one of: audio communication and video communication from the air module to at least one of the plurality of sealing and locking helmets.

19. The system of claim 1, further comprising a setup module in the memory comprising computer instructions to automatically create and display personnel profiles on the display, and the helmet module comprising: computer instructions to automatically display status of a lock out timer, computer instructions to automatically display user data tables with individual permissions of each user, and computer instructions instructing the air processor to add or delete users.

\* \* \* \* \*